(12) United States Patent
Giesen

(10) Patent No.: US 11,389,974 B2
(45) Date of Patent: Jul. 19, 2022

(54) REMOVABLE WRIST JOINT

(71) Applicant: Delaware Capital Formation, Inc., Wilmington, DE (US)

(72) Inventor: Isaac M. Giesen, Red Wing, MN (US)

(73) Assignee: Delaware Capital Formation, Inc., Wilmington, DE (US)

( * ) Notice: Subject to any disclaimer, the term of this patent is extended or adjusted under 35 U.S.C. 154(b) by 783 days.

(21) Appl. No.: 16/085,446

(22) PCT Filed: Mar. 16, 2017

(86) PCT No.: PCT/US2017/022763
§ 371 (c)(1),
(2) Date: Sep. 14, 2018

(87) PCT Pub. No.: WO2017/161150
PCT Pub. Date: Sep. 21, 2017

(65) Prior Publication Data
US 2020/0164528 A1 May 28, 2020

Related U.S. Application Data

(60) Provisional application No. 62/309,834, filed on Mar. 17, 2016.

(51) Int. Cl.
*B25J 17/02* (2006.01)
*B25J 21/00* (2006.01)
(Continued)

(52) U.S. Cl.
CPC ........... *B25J 17/0283* (2013.01); *A61B 34/70* (2016.02); *B25J 15/0206* (2013.01); *B25J 21/005* (2013.01); *A61B 2034/305* (2016.02)

(58) Field of Classification Search
CPC combination set(s) only.
See application file for complete search history.

(56) References Cited

U.S. PATENT DOCUMENTS

| 4,915,563 A | 4/1990 | Teillauchet et al. |
| 5,460,439 A | 10/1995 | Jennrich et al. |

(Continued)

FOREIGN PATENT DOCUMENTS

| EP | 0185568 | 6/1986 |
| EP | 0187871 | 7/1986 |

(Continued)

OTHER PUBLICATIONS

"Office Action," for Japanese Patent Application No. 2018-548715 dated Jan. 15, 2021 (9 pages) with English Translation.

(Continued)

*Primary Examiner* — Scott Luan
(74) *Attorney, Agent, or Firm* — Pauly, DeVries Smith & Deffner LLC

(57) ABSTRACT

A remote arm for a manipulator is disclosed, which has a boom tube having a distal end and housing a mechanical communication chain. A floating gearbox assembly is coupled to the boom tube and has an outer framework rigidly coupled to the distal end of the boom tube. An inner framework is retained by the outer framework and is rotatable relative to the outer framework. A drive gear is disposed in the inner framework, which is in mechanical communication with the mechanical communication chain. A wrist joint has a wrist joint housing and an output gear is disposed in the wrist joint housing, where the wrist joint housing is configured to detachably couple to the outer framework. The output gear is configured to mechanically communicate with (Continued)

the drive gear when the wrist joint housing is coupled to the outer framework.

17 Claims, 10 Drawing Sheets

(51) Int. Cl.
  *B25J 15/02* (2006.01)
  *A61B 34/00* (2016.01)
  *A61B 34/30* (2016.01)

(56) References Cited

U.S. PATENT DOCUMENTS

| | | |
|---|---|---|
| 2008/0042432 A1 | 2/2008 | Park et al. |
| 2012/0207538 A1 | 8/2012 | Rizk et al. |

FOREIGN PATENT DOCUMENTS

| | | |
|---|---|---|
| EP | 2772206 | 9/2014 |
| GB | 1599698 | 10/1981 |
| JP | S63102886 | 5/1988 |
| JP | 2733848 | 3/1998 |
| WO | 2010071808 | 6/2010 |
| WO | 2017161150 | 9/2017 |

OTHER PUBLICATIONS

"Response to Communication Pursuant to Rules 161(1) and 162 EPC," for European Patent Application No. 17715562.9 filed May 2, 2019 (13 pages).
"Installation, Operation and Maintenance Manual for the System 50 Master-Slave Manipulator," by Central Research Laboratories, Inc., Aug. 7, 1979 (105 pages).
"International Preliminary Reporton Patentability," for PCT Application No. PCT/US2017/022763 dated Sep. 27, 2018 (11 pages).
"International Search Report and Written Opinion," for PCT Application No. PCT/US2017/022763 dated Jun. 13, 2017 (17 pages).
"Communication Pursuant to Article 94(3) EPC," for European Patent Application No. 17715562.9 dated Apr. 23, 2021 (9 pages).
"Response to Communication Pursuant to Article 94(3) EPC," for European Patent Application No. 17715562.9 filed Aug. 12, 2021 (19 pages).

REMOVABLE WRIST JOINT

This application is being filed as a PCT International Patent application on Mar. 16, 2017 in the name of Delaware Capital Formation, Inc., a U.S. national corporation, applicant for the designation of all countries and Isaac M. Giesen, a U.S. Citizen, inventors for the designation of all countries, and claims priority to U.S. Provisional Patent Application No. 62/309,834, filed Mar. 17, 2016, the contents of which are herein incorporated by reference in its entireties.

FIELD OF THE TECHNOLOGY

The technology disclosed herein relates generally to a wrist joint and more particularly to a removable wrist joint.

BACKGROUND

In various industries it is preferable to work, test, assemble, and the like, in an environment that is isolated from ambient conditions. For example, in some medical and pharmaceutical applications, it may be preferable for such activities to occur in a substantially cleaner environment, where outside debris and bacteria cannot substantially affect conditions in the clean environment. In another example, it can be preferable for activities to be contained in a substantially dirtier environment, such as hot cells or laboratories, so inside waste does not substantially affect conditions on the outside. It is often necessary to have the capacity to manipulate devices, components, and the like, inside the isolated environment from the outside of the isolated environment without breaching the isolation of the environment itself. In various instances telemanipulators are used to conduct such activities.

Telemanipulators generally have a command arm that is mechanically, electrically, or hydraulically, or by using combinations of the three, connected to a remote arm. The remote arm is positioned on the inside of the isolated environment and the command arm is positioned outside of the isolated environment. The remote arm typically has an end effector, which can be a tong, for example, that interfaces with the contents of the isolated environment. An operator elicits and controls motion of the remote arm by maneuvering the command arm, and in many instances can perform quite complex tasks through the use of such a device. In such devices, it is often necessary to replace the end effector. In some instances this might be due to a need to use a different type of end effector, and in others this may be due to a perform maintenance on the current end effector. It is typically a slow and laborious process to access and replace an end effector because current designs require both the use of one or more tools and a user accessing the isolated environment. Often a second telemanipulator system is used to access the isolated environment to replace the end effector of the first telemanipulator system, which can be impractical for many reasons including cost and space restrictions. It is therefore desirable to provide a telemanipulator with an end effector that is relatively easily replaceable so that it does not require a user to breach the isolated environment or use another manipulator system for replacing an end effector.

SUMMARY

Some embodiments disclosed herein relate to a remote arm for a manipulator, which has a boom tube having a distal end and housing a mechanical communication chain. A floating gearbox assembly is coupled to the boom tube and has an outer framework rigidly coupled to the distal end of the boom tube. An inner framework is retained by the outer framework and is rotatable relative to the outer framework. A drive gear is disposed in the inner framework, which is in mechanical communication with the mechanical communication chain. A wrist joint has a wrist joint housing and an output gear is disposed in the wrist joint housing, where the wrist joint housing is configured to detachably couple to the outer framework. The output gear is configured to mechanically communicate with the drive gear when the wrist joint housing is coupled to the outer framework.

Some embodiments of the current technology relates to a method of coupling an end effector to a remote arm of a manipulator. A first coupling interface of a floating gearbox assembly of a remote arm is positioned in general axial alignment with a second coupling interface of an end effector. The first coupling interface of the floating gearbox assembly is extended to contact a second coupling interface defined by the end effector. The first coupling interface of the floating gearbox assembly is rotated relative to the second coupling interface of the end effector such that the floating gearbox assembly and the end effector mutually engage. Other embodiments are also described.

BRIEF DESCRIPTION OF THE DRAWINGS

The current technology may be more completely understood and appreciated in consideration of the following detailed description of various embodiments of the current technology in connection with the accompanying drawings.

DETAILED DESCRIPTION

Figure 1:
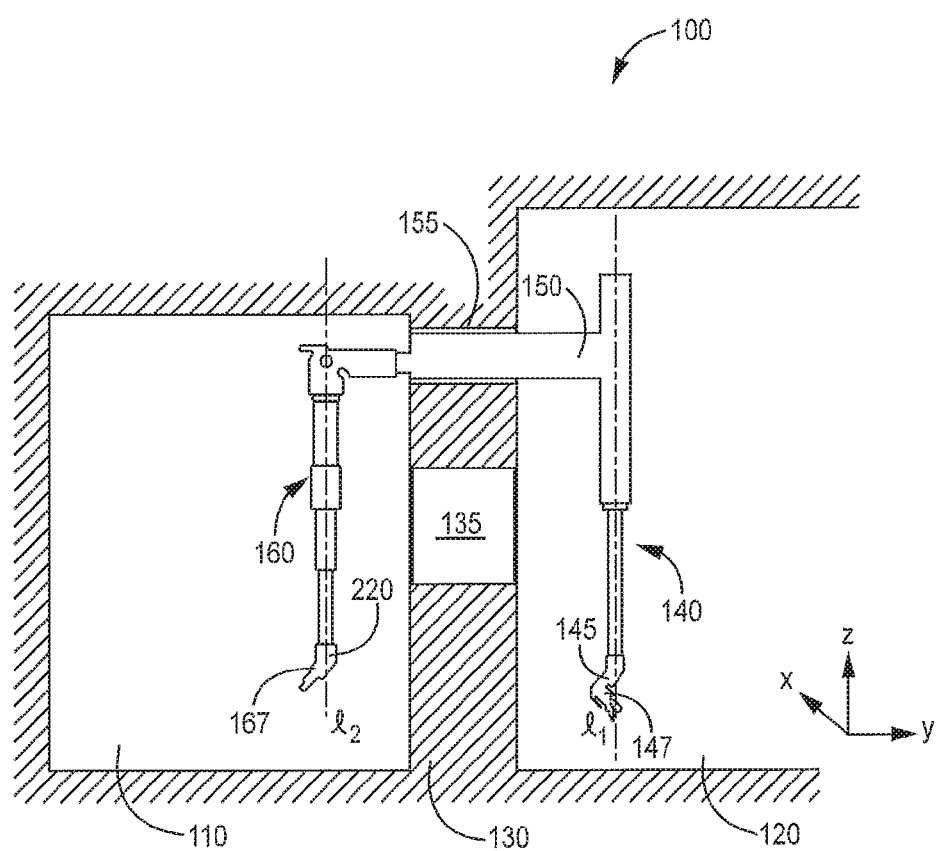
FIG. 1 is a schematic view of an example telemanipulator.

FIG. 1 is an example telemanipulator. Such a telemanipulator 100 is consistent with the technology disclosed throughout this application in various embodiments. The telemanipulator 100 broadly has three main components: a command arm 140, a remote arm 160, and a seal tube 150 that connects the command arm 140 to the remote arm 160. The remote arm 160 is in an isolated environment 110 for the purpose of manipulating content in the isolated environment 110. The command arm 140 is outside of the isolated environment 110, more specifically in a secondary environment 120 that is generally accessible to a user. The isolated environment 110 and the secondary environment 120 are separated by a wall 130 through which the seal tube 150 passes to connect the remote arm 160 to the command arm 140. The wall 130 can define a window 135 through which components in the isolated environment 110 can be viewed from the secondary environment 120.

The isolated environment 110 is, in a variety of embodiments, sealed off from the secondary environment 120 so that gases, debris, and the like cannot pass from one environment to the other, including around the seal tube 150 and the window 135. In some other embodiments, the isolated environment 110 is not sealed off from the secondary environment 120. The isolated environment 110 can be a hot cell, for example.

The telemanipulator 100 is configured so that when the command arm 140 is maneuvered in a particular manner ("directive motion") in the secondary environment 120, the remote arm 160 substantially responds with corresponding movements ("responsive motion") in the isolated environment 110. The command arm 140 can be directed in one or more of the X-axis, Y-axis, Z-axis, and Z-axis azimuth directions. The X-axis motion is defined by rotation of the command arm 140 about the Y-axis. The Y-axis motion is defined by rotation of the command arm 140 about the X-axis. The Z-axis motion is defined by linear motion along the longitudinal axis $l_1$ of the command arm 140. The Z-axis azimuth direction is rotation about the longitudinal axis $l_1$ of the command arm 140.

The command arm 140 has a command wrist joint 145 and a command handle 147 to further facilitate directive motions. The command arm 140 can incorporate a variety of triggers, buttons, switches, and the like for any number of commands that serve as directive input. Such triggers, buttons, switches, and the like can be disposed on the command handle 147. In some embodiments the command handle 147 incorporates a trigger that, when engaged, produces a grasping responsive motion in the remote arm 160. The command wrist joint 145 is positioned between the command handle 147 and the distal end of the command arm 140, and enables complex directive motions such as one or both of a rotational motion about an axis defined by the command wrist joint 145 and a pivot of the command handle 147 about the command wrist joint 145. In various embodiments the pivot of the command handle 147 about the command wrist joint 145 results in a slight lift of the command handle 147 relative to the command arm 140. The dual motions enabled by the command wrist joint 145 are collectively hereinafter referred to as the "elevation and twist" motion for purposes of this application.

The responsive motion of the remote arm 160 is likewise in one or more of the x-axis, y-axis, z-axis, and z-axis azimuth directions. The remote arm 160 has an end effector 167, which is a tong in the current embodiment, and a remote wrist joint 220 by which to facilitate responsive motions relative to the directive motions and/or directive inputs of the command arm 140. The remote wrist joint 220 is positioned between the distal end of the remote arm 160 and the end effector 167. Rotational motion of the end effector 167 is enabled about an axis defined by the remote wrist joint 220. Pivoting motion of the end effector 167 is enabled about the remote wrist joint 220. As mentioned above with regard to the command handle 147, the pivot of the end effector 167 about the remote wrist joint 220 results in a slight lift of the end effector 167 relative to the remote arm 160. Again, these dual motions enabled by the remote wrist joint 220 are also collectively hereinafter referred to as the "elevation and twist" motion for purposes of this application.

In various embodiments, the remote arm 160 is an independent remotely-removable unit that is interchangeable and couples with the seal tube 150. In some embodiments, the remote arm 160 couples to and uncouples from the seal tube 150 without breaking the seal between the isolated environment 110 and the secondary environment 120. In such embodiments the remote arm 160 can contain a self-aligning, self-locking mechanism for remotely coupling or uncoupling the remote arm 160 to or from the seal tube 150 from outside of the isolated environment 110. The end effector 167 can also be remotely removable and interchangeable with other types of end effectors.

The remote wrist joint 220 and the command wrist joint 145 are generally constructed so as to allow the elevation and twist motion as described above which is attainable through a variety of means known in the art. In various embodiments the wrist joint incorporates two gears and a yoke where the elevation and twist motion is driven by a chain that passes there through.

The command arm 140 is can be an independent, interchangeable, removable unit that couples to and uncouples from with the seal tube 150 without breaking the seal of the isolated environment 110. In some embodiments, the command arm 140 incorporates one or more of X-axis, Y-axis and Z-axis motion counterbalance weights for both the command arm 140 and remote arm 160.

The command handle 147 is generally configured for mechanical engagement by a user that causes a responsive grasping motion of the end effector 167. In some embodiments the mechanical engagement is the displacement of one handle component relative to another handle component, such as through pressing a trigger disposed on the handle or pivoting a handle gripping surface on the command handle 147. The command handle 147 can have a ratchet device or a locking device capable of maintaining engagement of the command handle to maintain the grasp of the end effector 167. In some example embodiments incorporating a ratchet, the ratchet is capable of being locked in or locked out of engagement. In some embodiments the command handle 147 has an adjustment screw to adjust the size of the grasp of the end effector 167 for handling objects of various widths. In multiple embodiments the command handle 147 has an adjustment screw to adjust the size of one or more gripping surfaces defined by the command handle 147 to accommodate the grip size sensation of a user operating the command handle 147.

The seal tube 150 is a sealed unit capable of transmitting directive motion from the secondary environment 120 to the isolated environment 110 while keeping the isolated environment 110 isolated. In a variety of embodiments, one or more seals are disposed within the seal tube 150 towards the command end of the seal tube 150. In some example embodiments, the space in between each pair of seals is filled with grease.

In at least one embodiment the seal tube 150 seals off the isolated environment 110 through a wall tube 155 that sealably extends through at least a portion of the wall 130 from the secondary environment 120 to the isolated environment 110. In a variety of embodiments, the seal tube 150 is sealably disposed within the wall tube 155. As an example, the seal tube 150 can be sealably disposed within the wall tube 155 with seals such as one or more nitrile rubber spring-loaded lip seals sealed towards the end of the wall tube 155 towards secondary environment 120. If multiple seals are used, the space between the seals can be filled with grease. Such a configuration allows the seal tube 150 to rotate within the wall tube 155 while maintaining the isolation of the sealed isolated environment 110. The seal tube 150 can be configured to engage command arms and remote arms having a variety of different configurations that can vary to fit the needs of particular applications.

In embodiments the seal tube 150 seals to the secondary environment 120 side of the wall 130. There can be a contamination barrier between the seal tube 150 and the wall tube 155, located on the isolated end of the seal tube 150. Such a contamination barrier can be consistent with those known in the art.

In some embodiments, the seal tube 150 mounts and seals to the inside diameter of the wall tube 155 towards the secondary environment 120 side of the wall tube 155. Such a seal can be a pair of neoprene, nitrile, and/or viton rings, for example, which are compressed axially and expand to seal the seal tube 150 assembly to the inside diameter of the wall tube 155.

In some, but not all, embodiments the manipulator 100 has motor-driven movements in the X, Y and Z directions that is accessed through manually operated switches in the secondary environment 120 that provide directive input to the remote arm 160 by engaging a motor. Such motor-driven movements can be referred to as "indexing." The motor can be an electrical motor, but other types of motors are certainly contemplated. The X-axis motion is defined by rotation of the remote arm 160 about the Y-axis. In some embodiments the remote arm 160 can be indexed up to 45° in either X-axis direction relative to the command arm 140. The Y-axis motion is defined by rotation of the remote arm 160 about the X-axis. In some embodiments the remote arm 160 is capable of being indexed from 90° to −150 relative to the remote arm 160 position perpendicular to the plane defined by the X-axis and the Y-axis, where a positive angle is defined as movement away from the wall 130. The Z-axis motion is defined by linear motion along the longitudinal axis $l_2$ of the remote arm 160. Depending on the orientation of the remote arm 160, extension or retraction of the remote arm 160 along its longitudinal axis $l_2$ will not always be aligned with the Z-axis in space. However, for purposes of this application, extension or retraction of the remote arm 160 along its longitudinal axis $l_2$ shall be referred to as being in the Z direction. In some embodiments, the motor is capable of lifting 100 pounds (45 kg).

Responsive motion in the end effector 167 is initiated through a mechanical communication chain that transmits the directive motion originating at the command handle 147 to the end effector 167. Directive inputs, which are generally indexed movements described above, can be disposed on the command arm 140, but are generally accessible from the command handle 147 and thus are referred to as being inputted from the command handle 147 for purposes of this application. Furthermore, for purposes of this application, the combination of elements that contribute to the responsive motion of the end effector 167 in response to directive motions and inputs of the command handle 147 are referred to as mechanical communication chains. In various embodiments the mechanical communication chain is a substantially mechanical system that can incorporate electronic elements. In some embodiments the mechanical communication chain is a substantially electronic system that incorporates mechanical elements. Such mechanical communication chains generally begin from a directive motion or directive input at the command handle 147 and eventually leads to corresponding responsive motion of the end effector 167.

The mechanical communication chains have a variety of gears, pulleys, chains, cables, tapes, belts, drums, motors, links, and the like that are configured to receive directive motions and directive inputs from the command handle 147 to elicit responsive motion of the end effector 167. For purposes of this application, any means of transmitting power from a rotational source to a rotational receiver using a continuous loop of material will be referred to as a tape, and any source or receiver capable of mechanically communicating with such a tape will be referred to as a drum. Examples of tapes include chains, cables, ropes, strings, belts, tapes, and the like. Examples of drums include pulleys, cogs, gears, sprockets, drums, and the like.

Generally each axis of motion available to the end effector 167 has a particular mechanical communication chain associated with it. A first mechanical communication chain is configured to direct the end effector 167 along a first axis in response to a directive motion of the command handle 147. The first axis can be the X-axis in multiple embodiments. A second mechanical communication chain is further configured to direct the end effector 167 along a second axis in response to the directive motion of the command handle 147. In various embodiments the second axis is the Y-axis. A third mechanical communication chain is configured to direct the end effector 167 along a third axis in response to the directive motion of the command handle 147, which can be the Z-axis. A fourth mechanical communication chain is configured to direct the end effector 167 about the third axis in response to the directive of the command handle 147, which can correspond to a Z-axis azimuth responsive motion.

The movement associated with the electrically-driven indexing in the X, Y, and Z directions can be accessed through manually operated switches from the command handle 147 that provide directive input by engaging a motor. In various embodiments the motor is an electrical motor. The motor is a component in at least one mechanical communication chain to elicit responsive motion of the end effector 167 from the directive input of at least one switch, toggle, trigger, or the like, of the command handle 147.

In some example embodiments, the command end of the seal tube 150 has a split seal plate, for example, mounted therein that holds one or more scaling components abutting each mechanical communication chain. In some embodiments the sealing components are a pair of nitrile rubber spring-loaded lip seals for each mechanical communication chain.

Figure 2:
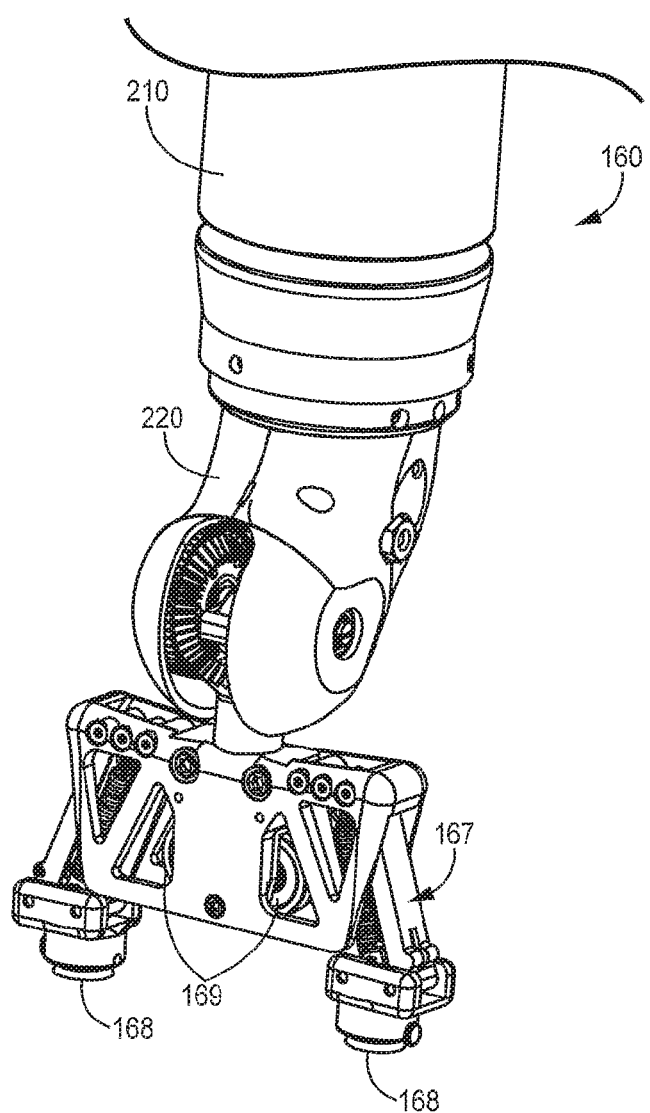
FIG. 2 is a perspective view of an example remote wrist joint.
Figure 3:
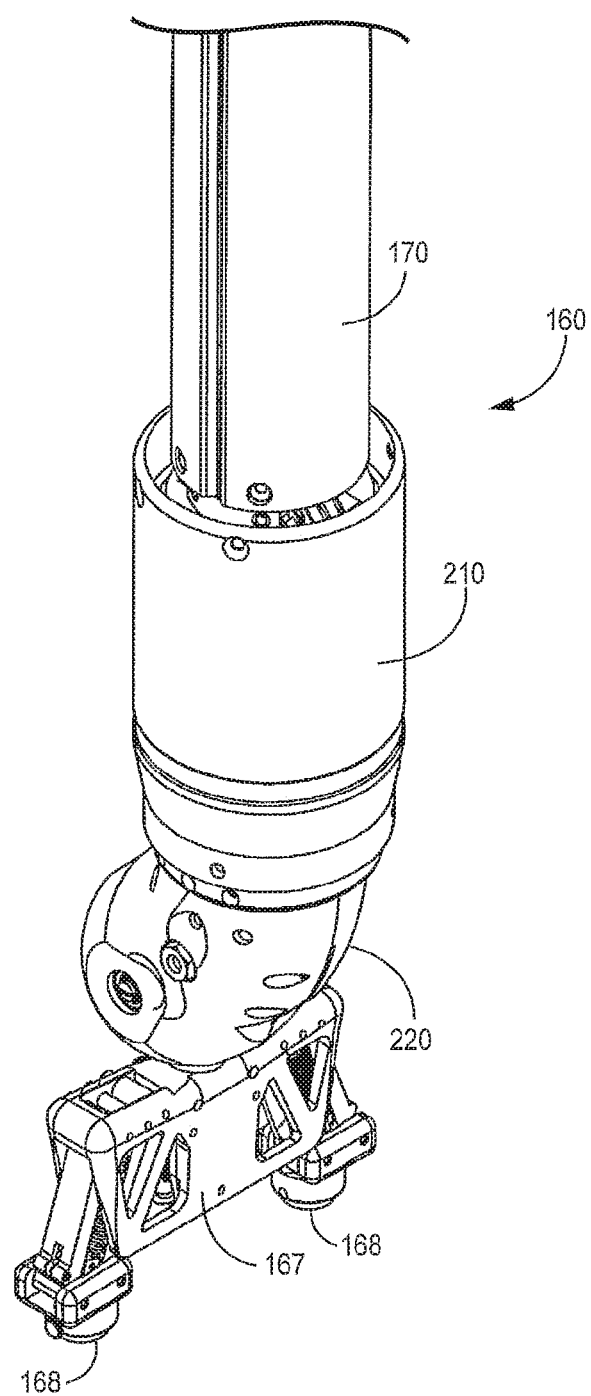
FIG. 3 is a perspective view of the example wrist joint of FIG. 2 from another perspective.

FIG. 2 shows a perspective view of an example distal end of a remote arm 160 consistent with embodiments disclosed herein, and FIG. 3 shows the distal end of the remote arm 160 from a different perspective. The distal end of the remote arm 160 has a boom tube 170, a floating gearbox assembly 210, a wrist joint 220, and a end effector 167. In the current embodiment, the floating gearbox assembly 210 is fixed to the boom tube 170 and the end effector 167 fixed to the remote wrist joint 220. In a variety of embodiments the remote wrist joint 220 is removably coupled to the floating gearbox assembly 210.

The boom tube 170 can have a variety of configurations, but generally extends from the distal end of the remote arm 160 towards the seal tube (see FIG. 1). The boom tube 170 is generally configured to house a length of each of the mechanical communication chains extending from the command handle 147 to the end effector 167. The boom tube 170 can be a single component or can be multiple components joined together.

The end effector 167 is generally the component that interfaces with materials contained in the isolated environment. The end effector 167 can have jaws 168 that can be configured to grasp materials. The end effector 167 can be configured to execute responsive motion relative to the remote wrist joint 220 and/or other components. In some embodiments the end effector 167 has the ability to rotate relative to the remote wrist joint 220. In many embodiments, the end effector is a tong, as has been described herein, and in some embodiments the end effector can be a tool. For example, the end effector can be a screwdriver configured to rotate in response to rotation of the output gear. In another example, the end effector can be a wrench. In various embodiments the end effector is configured to translate rotational motion—such as gear rotation—into mechanical work.

The wrist joint 220 has a wrist joint housing 402 that houses one or more mechanical communication chains that extend to the end effector 167 to elicit responsive motion in the end effector 167. For example, in some embodiments the wrist joint 220 translates mechanical movement resulting in a grasping responsive motion of the end effector 167 that was initiated from directive motion or input at the command handle 147. In some embodiments the wrist joint 220 transmits Z-axis azimuth motion of the end effector 167 that was initiated from directive motion or input at the command handle 147.

The floating gearbox assembly 210 and the wrist joint 220 are configured to reversibly mutually engage. The floating gearbox assembly 210 serves as an interface between the boom tube 170 and the wrist joint 220. The floating gearbox assembly 210 and the wrist joint 220 can mutually engage through a variety of alternate means. In some embodiments, the floating gearbox assembly 210 and the wrist joint 220 have mating features that are configured to mutually engage. As an example, the floating gearbox assembly 210 and the wrist joint 220 defines threaded surfaces that are configured to mutually engage upon rotation. As another example, the floating gearbox assembly 210 and the wrist joint 220 are configured to clamp together with the application of pressure relative to each other. As yet another example the floating gearbox assembly 210 and the wrist joint 220 defines a snap-fit to engage with the application of pressure.

In some embodiments, the wrist joint 220 is removably coupled to the floating gearbox assembly 210 with a bayonet style connection. In such embodiments the connection can be disengaged by rotating the floating gearbox assembly 210 relative to the wrist joint 220 in a first direction and translating the gearbox assembly 210 axially away from the wrist joint 220 by retracting the remote arm 160 in the Z direction. In some embodiments, the connection between the wrist joint 220 and the floating gearbox assembly 210 can be engaged by rotating the floating gearbox assembly 210 relative to the wrist joint 220 in a second direction opposite from the first direction and translating the floating gearbox assembly 210 axially inward toward the wrist joint 220. Other means of removably coupling the wrist joint 220 with the floating gearbox assembly 210 can be used. Various types of connections that enable the rapid and simple coupling of the components are contemplated.

Figure 4:
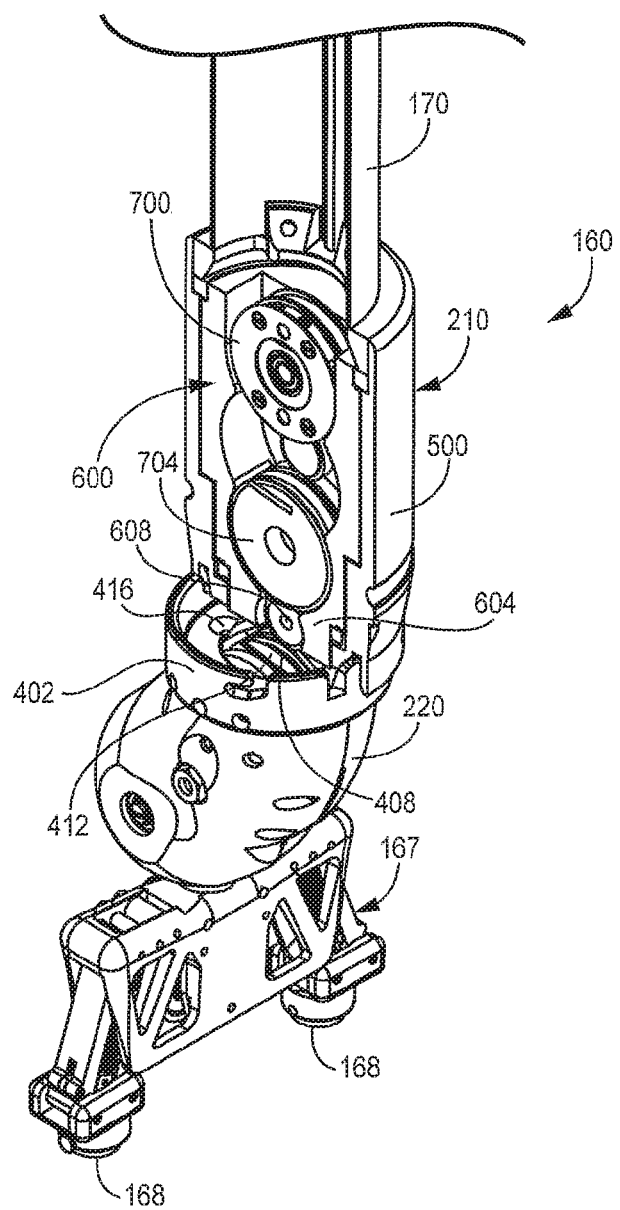
FIG. 4 is a perspective sectional view of the example wrist joint of FIG. 3.

FIG. 4 is sectional perspective view of the remote arm 160 from the same perspective as FIG. 3, with a section of the floating gearbox assembly 210 and the boom tube 170 removed. The floating gearbox assembly 210 has an outer framework 500 and a floating gearbox 600. The floating gearbox 600 is disposed within the outer framework 500. The floating gearbox 600 defines at least a portion of one or more mechanical communication chains. In some embodiments, the mechanical communication chains have input tape drums 700 that are in communication with drive gears 608. The input tape drums 700 are in communication with the drive gears 608 through idler gears 704. The floating gearbox 600 has an inner framework 604 that is rotatable within the outer framework 500 of the floating gearbox assembly 210. Bearings can be disposed between the inner framework 604 and the outer framework 500 to enable relative rotation of the inner framework 604 and the outer framework 500.

A drive gear 608 disposed in the inner framework 604 has an axle 609 that is fixed to the inner framework 604. Similarly, an input tape drum 700 disposed in the inner framework 604 has an axle fixed to the inner framework 604. Also, an idler gear 704 disposed in the inner framework 604 has an axle fixed to the inner framework 604. In various embodiments, rotational components can share a common axle.

The outer framework 500 of the floating gearbox assembly 210 is generally fixed to the boom tube 170. The outer framework 500 of the floating gearbox assembly 210 is configured to removably receive the wrist joint 220. The outer framework 500 and the wrist joint 220 generally define a coupling interface. In various embodiments, the wrist joint 220 has a wrist joint housing 402 defining a bayonet connector 406 and the outer framework defines a mating bayonet connector 504 such that the wrist joint 220 and the outer framework 500 detachable couple. The bayonet connector 406 is one or more bayonet receptacles that are configured to receive corresponding bayonet protrusions 504 defined by the outer framework 500. In some embodiments the bayonet connector is one or more bayonet protrusions that are configured to be received by corresponding receptacles defines by the outer framework 500. Other types of interfaces can be defined, as well.

When the floating gearbox assembly 210 and the wrist joint 220 are coupled, the drive gears 608 of the floating gearbox 600 are configured be in alignment with output gears 408, 412 of the wrist joint 220. In some embodiments, where the end effector 167 is a tong, the output gears 408, 412 of the wrist joint 220 are at least an elevation and twist gear output gear 408 that affects the elevation and twist motion of the end effector and/or a grasping gear 412 that affects the grasping motion of the jaws of the tong. For purposes of this application, a "gear" used herein refers to any structure capable of transmitting motion along a mechanical communication chain between the command handle 147 and the end effector 167. As examples, a gear can be a toothed or cogged wheel, a friction wheel, and the like.

In a variety of embodiments, the wrist joint housing 402 and the floating gearbox assembly 210 mutually define an alignment interface to ensure proper alignment of the wrist joint housing 402 and the floating gearbox assembly 210 and their corresponding mechanical communication chains. The alignment interface can have a variety of configurations. In some embodiments, one of the wrist joint housing 402 and the inner framework 604 of the floating gearbox assembly 210 defines a timing pin and the other of the wrist joint housing 402 and the inner framework 604 of the floating gearbox assembly 210 defines a timing pin receptacle. The alignment interface can particularly enable radial alignment between the inner framework 604 and the wrist joint 220.

In the embodiment depicted in FIG. 4, the wrist joint 220 defines a timing pin receptacle 416. The timing pin receptacle 416 is configured to receive a timing pin (not shown) from the floating gearbox assembly 210. The timing pin receptacle 416 can be a hole, tapered hole, slot, tapered slot, or other recessed geometry that is configured to guide the timing pin towards an engaged and aligned position within the timing pin receptacle 416. The use of the timing pin receptacle 416 is discussed in further detail in the descriptions of subsequent figures.

When the timing pin is fully engaged by the timing pin receptacle 416, the wrist joint housing 402 and the floating gearbox assembly 210 are coupled. When the timing pin is fully engaged by the timing pin receptacle 416 the floating gearbox 600 is prevented from rotating about the Z-axis relative to the wrist joint housing 402 and the outer framework 500. When the timing pin is fully engaged by the timing pin receptacle 416 the drive gears 608 of the floating gearbox 600 are configured to be in mechanical communication with corresponding gears of the wrist joint 220.

The input tape drums 700 of the floating gearbox 600 are configured to be in mechanical communication with the command handle 147 (depicted in FIG. 1) through a mechanical communication chain. The mechanical communication chain can be at least partially defined by tape extended over drums in some embodiments. As such, the mechanical communication chains extending from the boom tube 170 to the floating gearbox 600 to the wrist joint 220 can be relatively tolerant to misalignment between the input tape drums 700 of the floating gearbox 600 and adjacent drums in the boom tube 170. In some embodiments, the tape can bias the floating gearbox 600 tape drums 700 to be relatively aligned with adjacent drums in the mechanical communication chain.

Figure 5:
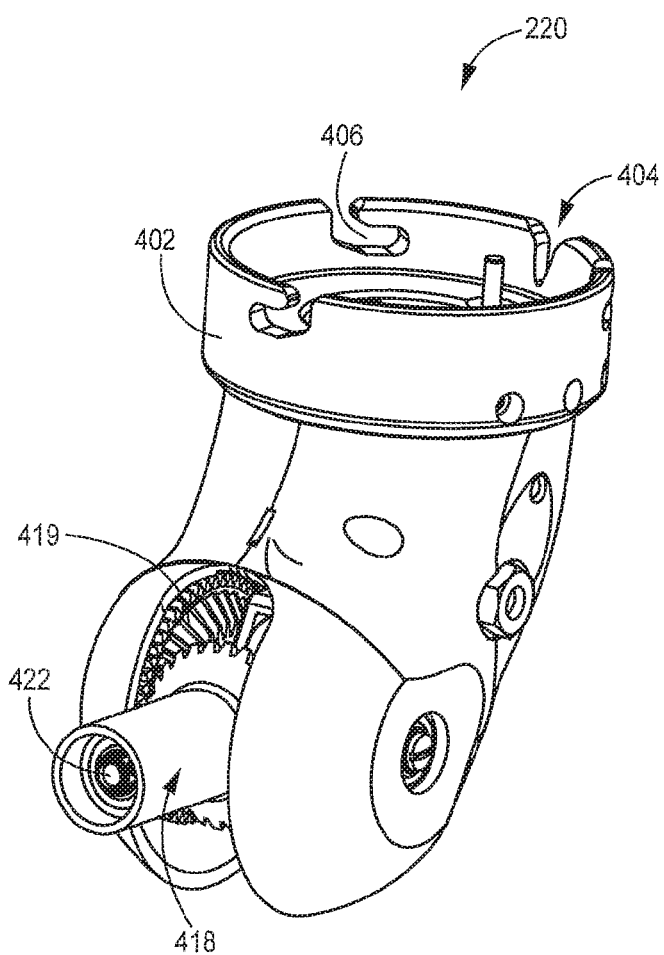
FIG. 5 is a perspective view of a wrist joint consistent with the technology disclosed herein.
Figure 6:
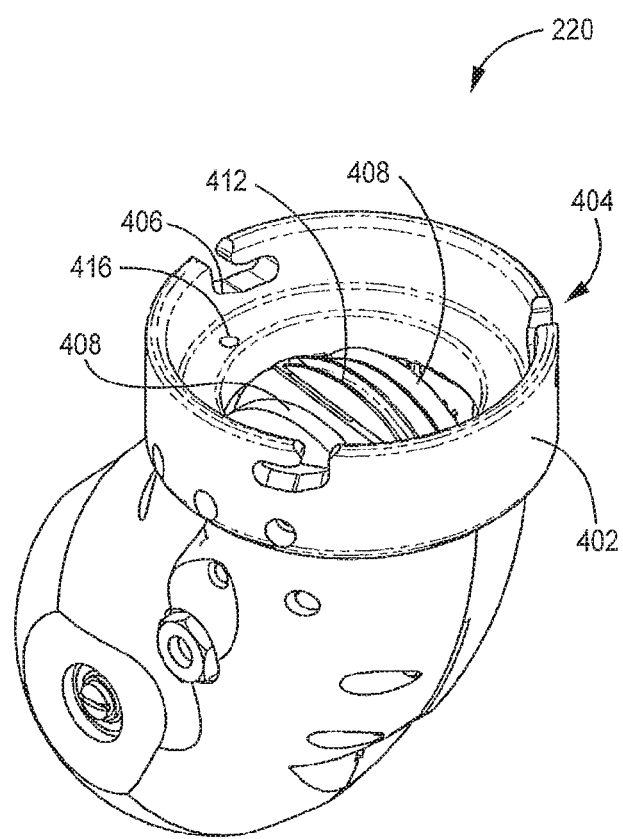
FIG. 6 is a perspective view of the wrist joint of FIG. 6 from another perspective.

FIGS. 5 and 6 are perspective views of an example wrist joint 220 consistent with FIGS. 2-4. The wrist joint 220 has a wrist joint housing 402. The wrist joint housing 402 defines one or more bayonet connectors 404. In the current embodiment, the bayonet connector 404 is a plurality of bayonet receptacles 406 that are configured to receive corresponding bayonet protrusions. In some embodiments the bayonet connectors can define bayonet protrusions that are configured to be received by corresponding bayonet receptacles. In some examples, wrist joint housing 402 can define threads or other connector means for coupling with the floating gearbox assembly 210 in lieu of a bayonet connector.

The wrist joint 220 has one or more output gears 408, 412 that are configured for mechanical communication with drive gears of the floating gearbox assembly 210. In some embodiments, one or more output gears are wrist elevation and twist output gears 408. In this example, the wrist joint 220 has two elevation and twist output gears 408. Motion of the output gears 408 relative to each other and relative to the wrist joint housing 402 affects the elevation and twist motions of the end effector 167. In particular, the motion of the elevation and twist output gears 408 of the wrist joint 220 is transmitted through a mechanical communication chain to the end effector 167 (FIG. 5). In the current embodiment, this mechanical communication chain has corresponding intermediate transmission gears 419 (only one is visible in FIG. 5) in rotational communication with a bevel gear 418 of the end effector 167. The bevel gear 418 drives the elevation and twist of the end effector 167. Alternate particular configurations are contemplated.

In the current embodiment, at least one output gear is a grasping gear 412. The grasping gear 412 is configured to interface with a drive gear on the floating gearbox assembly 210. The motion of the grasping gear 412 relative to the wrist joint housing 402 affects the opening and closing of the jaws of the end effector 167. In various embodiments, the motion of the grasping gear 412 is transmitted through a mechanical communication chain to the jaws 168 of the end effector 167 to open and close in a grasping motion. In this particular embodiment, this mechanical communication chain has an output cable 422 that is in communication with the grasping gear 412 and extends through the bevel gear 418 to the end effector 167. The output cable 422 can split at the bevel gear and each end of the output cable 422 can extend to each jaw 168 via corresponding jaw pulleys 169 (see FIG. 2). The output cable 422 drives the end effector 167 jaws 168 to open and close in a grasping motion. Alternate particular configurations are contemplated.

Figure 7:
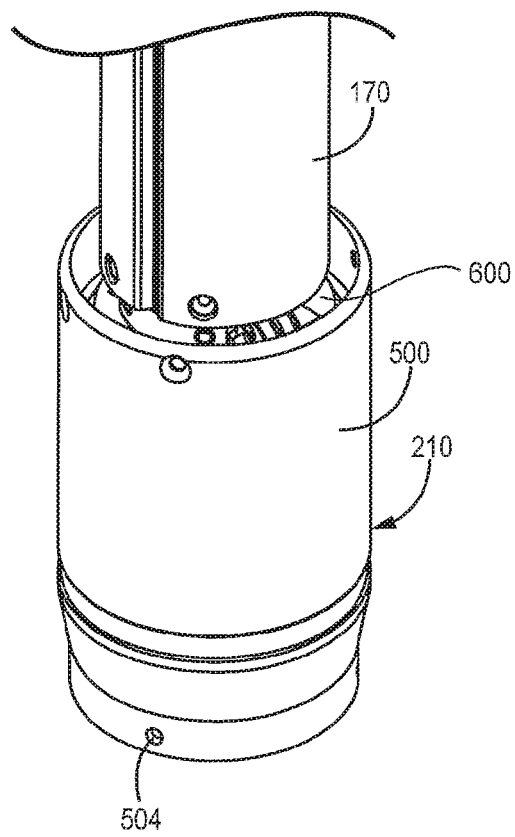
FIG. 7 is a perspective view of a boom tube and floating gearbox assembly consistent with the technology disclosed herein.
Figure 8:
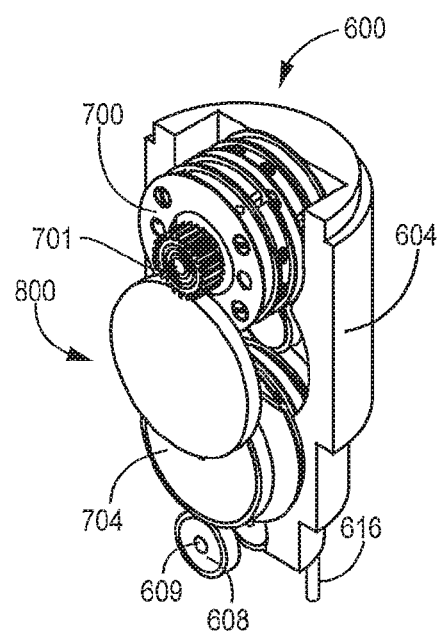
FIG. 8 is a perspective view of a partial floating gearbox assembly.
Figure 9:
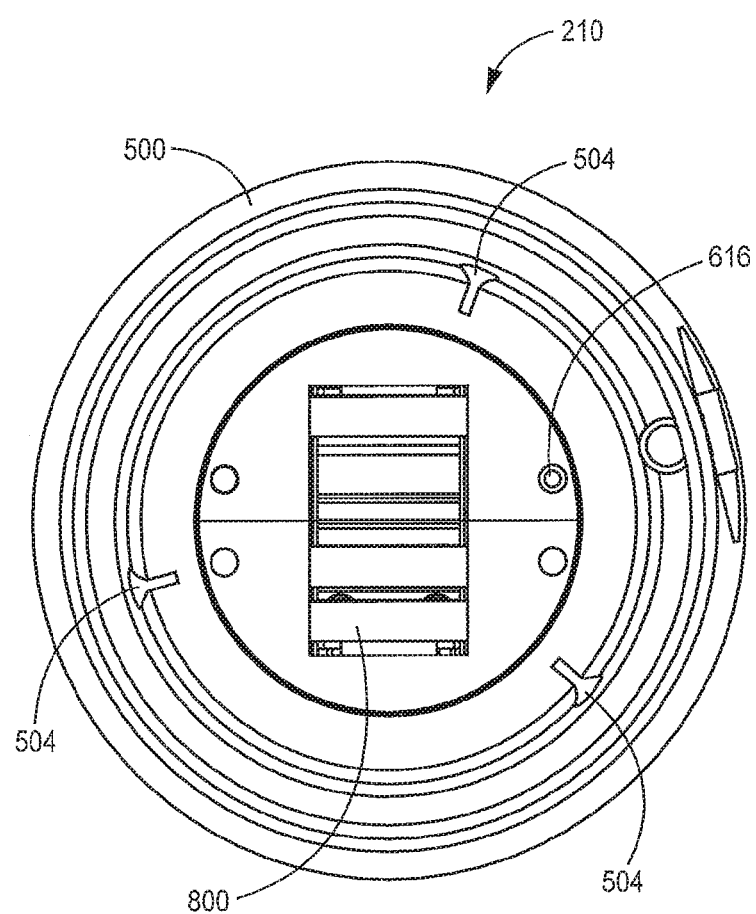
FIG. 9 is a bottom view of a floating gearbox assembly consistent with the technology disclosed herein.

FIG. 7 is a perspective view of the manipulator boom tube 170 and the floating gearbox assembly 210, and FIG. 8 is a perspective sectional view of the floating gearbox 600. FIG. 9 is a bottom plan view of the floating gearbox assembly 210. The floating gearbox assembly 210 has an outer framework 500 and a floating gearbox 600 disposed therein. The outer framework 500 is a generally cylindrical tube that shrouds the floating gearbox 600 and retains it therein. The outer framework 500 defines bayonet connectors configured to receive mating bayonet connectors of the wrist joint 220. In the current embodiment, the bayonet connectors are a plurality of radial inwardly oriented bayonet protrusions 504 that correspond to the plurality of bayonet receptacles 406 defined by the wrist joint 220. In some examples, the floating gearbox assembly 210 can have threads or other structures for mating with a corresponding wrist joint 220 in lieu of bayonet protrusions 504.

The floating gearbox 600 has an inner framework 604 and at least a portion of one or more mechanical communication chains 800 disposed within the inner framework 604. In some examples, the floating gearbox housing 500 has two halves or clamshells that are joined with coupling hardware such as screws. The floating gearbox housing 500 has a timing pin 616 extending therefrom, which is configured for receipt by a timing pin receptacle 416 of the wrist joint 220 (See FIG. 6). The timing pin 616 is configured to mate with the timing pin receptacle 416 when the floating gearbox assembly 210 is coupled to the wrist joint 220.

The floating gearbox 600 is free to rotate in the azimuth direction relatively independently from the outer framework 500. In a variety of embodiments one or more bearings are disposed between the outer framework 500 and the floating gearbox 600. In some embodiments the tape extending through the boom tube 170 and the tape drums of the floating gearbox 600 is generally rigid with the boom tube 170. The tape can be under enough tension to retain the position of the input tape drums 700 and the floating gearbox 600 relative to the boom tube 170 and the outer framework 500 until a greater opposing force is applied.

The floating gearbox 600 has a plurality of drive gears 608 that are configured to mechanically communicate with the elevation and twist output gears 408 and the grasping gear 412 of the wrist joint 220 when the two are in a coupled state. Each drive gear 608 is configured to be in mechanical communication with one corresponding output gear on the wrist joint 220 when the two components are properly aligned by the timing pin 616 and timing pin receptacle 416, by the bayonet connectors, or by other means. The drive gears are each in mechanical communication with the command handle 147 through one or more mechanical communication chains.

Figure 10:
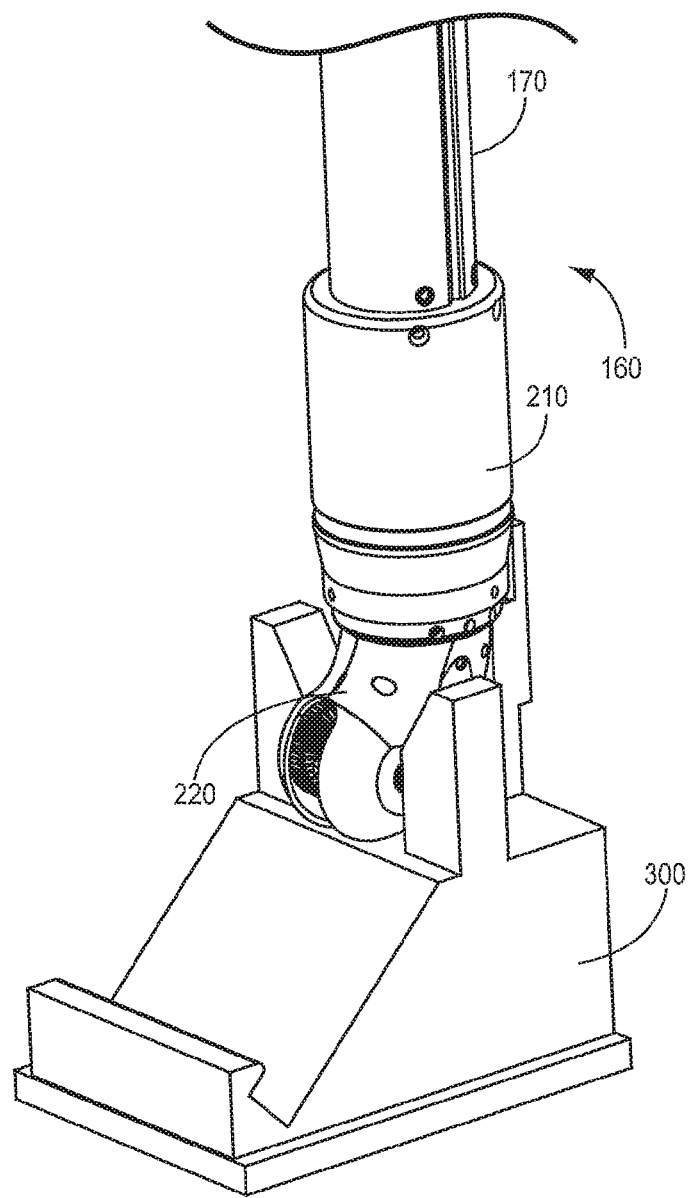
FIG. 10 is a perspective view of the remote wrist joint of FIG. 2 inserted into a restraining fixture.
Figure 11:
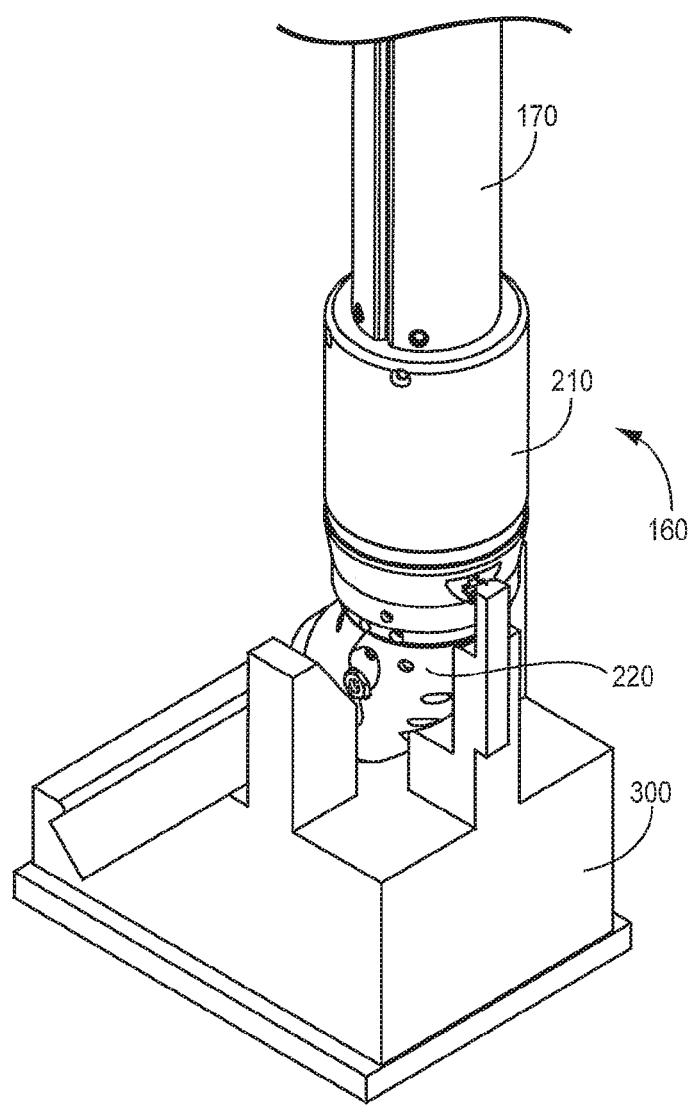
FIG. 11 is a perspective view of the remote wrist joint inserted into the restraining fixture from another perspective.

FIGS. 10 and 11 depict the wrist joint 220 of FIG. 2 (without an end effector) placed into a restraining fixture 300. The restraining fixture 300 is used to restrain the end effector and attached wrist joint 220 to facilitate the coupling to and uncoupling from the wrist joint 220 and the floating gearbox assembly 210. The fixture 300 is placed inside the isolated environment 110 (FIG. 1) in a location accessible by the end effector 167 and wrist joint 220. A user directs the end effector 167 into the fixture such that the end effector 167 and wrist joint 220 arc substantially restrained, meaning that the end effector 167 and the wrist joint 220 are prevented from translating in the X and Y directions and from rotating in the Z-axis azimuth direction. The user can uncouple the wrist joint 220 and the floating gearbox assembly 210 through a directive motion/input on the command side of the manipulator, resulting in rotation of the end effector 167 in a first Z-axis azimuth direction. Because the wrist joint 220 is retained by the fixture 300, the torque applied to the outer framework 500 of the floating gearbox assembly 210 will rotate with respect to the wrist joint 220 in such a manner so as to disengage from the wrist joint 220. There can be some rotation of the outer framework 500 relative to the floating gearbox 600, as well, because the tape extending from the boom tube 170 to the tape drums in the floating gearbox 600 can bias the floating gearbox 600 such that the tape drums remain aligned relative to the rotated outer framework 500.

The recoupling of the wrist joint 220 with the floating gearbox assembly 210 can be performed in a manner similar to the removal. A user provides directive motion/input on the command side of the manipulator to (1) bring the floating gearbox assembly 210 in general axial alignment with the wrist joint, (2) axially lower the floating gearbox assembly 210 on to the wrist joint 220, and then to (3) rotate the floating gearbox assembly 210 in a second Z-axis azimuth direction (opposite from the first Z-axis azimuth direction) so the floating gearbox assembly 210 and the wrist joint 220 mutually engage.

Although a skilled operator can position the floating gearbox assembly 210 such that it is generally aligned with the wrist joint 220, there will generally be some misalignment between the drive gears 608 (See FIG. 8, for example) of the floating gearbox assembly 210 and the mating output gears 408, 412 (See FIG. 6, for example) of the wrist joint 220 that is difficult to perceive. As such, the timing pin 616 (FIGS. 8 and 9) of the floating gearbox 600 and the timing pin receptacle 416 (FIG. 6) of the wrist joint 220 are configured to mate upon proper alignment between the floating gearbox assembly 210 and the wrist joint 220. In some embodiments the floating gearbox assembly 210 and the wrist joint 220 are configured to mutually engage in a manner that results in proper alignment between the floating gearbox assembly 210 gears and the wrist joint 220 gears.

In a variety of embodiments, when the timing pin 616 (FIG. 8) is placed within an outer perimeter region of the timing pin receptacle 416 (FIG. 6), the floating gearbox assembly 210 and the wrist joint 220 can be coupled. The operator extends the boom tube 170 downward in the Z direction (and in the X and Y directions, as necessary) until the floating gearbox assembly 210 contacts a mating surface of the wrist joint 220. If the timing pin 616 does not make contact with the outer perimeter region of the timing pin receptacle 416, the operator provides directive input in the Z-axis azimuth direction until the timing pin 616 is positioned within the outer perimeter region of the timing pin receptacle 416. If the timing pin 616 is under pressure between the wrist joint 220 and the boom tube 170, the outer perimeter region of the timing pin receptacle 416 is configured to guide the timing pin 616 towards the inner region of the timing pin receptacle 416. In one example, the timing pin 616 follows the taper of the outer perimeter region towards a central opening of the timing pin receptacle 416. This point in the process is referred to as pin capture. In some embodiments, the timing pin 616 has been captured once it has been received by the timing pin receptacle 416.

After the pin has been successfully captured, an operator engages the connection between the outer framework 500 and the wrist joint 220 in a manner consistent with that described above. The operator provides directive motion/input to rotate the boom tube 170 in the azimuth direction until the bayonet connectors of the floating gearbox assembly 210 are aligned with the bayonet connectors of the wrist joint 220. The floating gearbox 600 maintains its alignment with the wrist joint 220 because the captured timing pin 616 provides a force opposing the rotation of the floating gearbox 604 with the boom tube 170 and tape. In some embodiments, the operator lowers and rotates the floating gearbox assembly 600 such that the bayonet protrusions 504 of the outer framework 500 are received by the bayonet receptacles 406 defined by the wrist joint 220. The operator then rotates the boom tube in the second Z-axis azimuthal direction until the bayonet protrusions 504 fully engage the bayonet receptacles 406. The locking of the bayonet connection causes the floating gearbox 600 to be fully lowered onto the wrist joint 220, thus fully engaging the timing pin 616 with the timing pin receptacle 416. The full engagement of the timing pin 616 with the timing pin receptacle 416 causes the floating gearbox 600 to be in proper alignment with the wrist joint 220 and the mechanical communication chain in the boom tube 170. When the floating gearbox assembly is engaged with the wrist joint 220, one or more mechanical communication chains are completed between the end effector 167 and the command handle 147 (FIG. 1).

By placing one or more fixtures in the isolated environment, the removal and replacement of end effectors can be performed relatively rapidly, and without the use of another manipulator system. In some embodiments, disparate fixtures corresponding to disparate end effectors enable a user to selectively couple to an end effector that suits a particular need at the time of use. In some examples of use, a user may need to remove an end effector in need of maintenance and couple to one of a plurality of available end effectors so that operation of the manipulator can continue without necessitating a user's accessing the isolated environment to perform immediate maintenance. In some embodiments, it can be desirable to replace an end effector that has particular functionality with a different type of end effector that has different functionality. For example, a tong can be replaced with a screwdriver, a ratchet, or a wrench, as examples. In various embodiments, each fixture can restrain one or more end effectors of like or disparate design.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

What is claimed is:

1. A remote arm of a manipulator comprising:
   a boom tube having a distal end, wherein the boom tube houses a mechanical communication chain;
   a floating gearbox assembly coupled to the boom tube, the floating gearbox assembly comprising:
      an outer framework rigidly coupled to the distal end of the boom tube,
      an inner framework retained by the outer framework, wherein the inner framework is rotatable relative to the outer framework, and
      a drive gear disposed in the inner framework, wherein the drive gear is in mechanical communication with the mechanical communication chain; and
   a wrist joint having a wrist joint housing and an output gear disposed in the wrist joint housing, wherein the wrist joint housing is configured to detachably couple to the outer framework by rotating the outer framework relative to the wrist joint, and the output gear is configured to mechanically communicate with the drive gear when the wrist joint housing is coupled to the outer framework.

2. The remote arm of claim 1, wherein the drive gear comprises an axle that is fixed to the inner framework.

3. The remote arm of claim 1, wherein the wrist joint housing defines a bayonet connector and the outer framework defines a mating bayonet connector whereby the wrist joint and the outer framework detachably couple.

4. The remote arm of claim 1, further comprising an alignment interface mutually defined by the inner framework and the wrist joint housing, wherein the alignment interface enables radial alignment between the inner framework and the wrist joint.

5. The remote arm of claim 1, wherein the alignment interface comprises a timing pin and a timing pin receptacle.

6. The remote arm of claim 1, further comprising an end effector coupled to the wrist joint and in mechanical communication with the output gear, wherein the end effector is configured to translate rotational motion to mechanical work.

7. The remote arm of claim 6, wherein the end effector is a tong that comprises jaws configured to pivot towards each other and away from each other in response to rotation of the output gear.

8. The remote arm of claim 6, wherein the end effector is a tong that is configured to rotate in response to rotation of the output gear.

9. The remote arm of claim 6, wherein the end effector is a screwdriver configured to rotate in response to rotation of the output gear.

10. The remote arm of claim 1, wherein the wrist joint housing is configured to detachably couple to the outer framework by rotating the outer framework relative to the inner framework.

11. A method of coupling an end effector to a remote arm of a manipulator comprising:
    positioning a first coupling interface of a floating gearbox assembly of the remote arm in general axial alignment with a second coupling interface of an end effector, wherein the floating gearbox assembly comprises an inner framework and an outer framework defining the first coupling interface;
    extending the first coupling interface of the floating gearbox assembly to contact a second coupling interface defined by the end effector; and
    transmitting one of: directive motion and directive input through a mechanical communication chain extending from a command side of the manipulator to the remote arm to rotate the first coupling interface of the floating gearbox assembly relative to the second coupling interface of the end effector by rotating the outer framework relative to a wrist joint of the end effector such that the floating gearbox assembly and the end effector mutually engage.

12. The method of claim 11, wherein the first coupling interface and the second coupling interface define a bayonet connection.

13. The method of claim 11, wherein rotating the first coupling interface of the floating gearbox assembly relative to the end effector further couples an alignment interface mutually defined by the floating gearbox assembly and the end effector.

14. The method of claim 13, wherein the alignment interface comprises a timing pin and a timing pin receptacle.

15. The method of claim 13, wherein the alignment interface is mutually defined by an inner framework of the floating gearbox assembly, and coupling the alignment interface prevents the inner framework from rotating relative to the end effector.

16. The method of claim 11, further comprising receiving at least one directive in the group consisting of: directive motion and directive input from the command side to position the first coupling interface and extend the first coupling interface.

17. The method of claim 11, wherein the end effector is configured to translate rotational motion to mechanical work.

* * * * *